United States Patent [19]
Newsome

[11] Patent Number: 6,101,411
[45] Date of Patent: Aug. 8, 2000

[54] DILATION ENHANCER

[76] Inventor: David A. Newsome, 18 Park Island Dr., New Orleans, La. 70122

[21] Appl. No.: 09/160,106

[22] Filed: Sep. 24, 1998

[51] Int. Cl.[7] .............................. A61N 1/30; A61N 1/00; A61M 35/00; A61B 5/04

[52] U.S. Cl. .......................... 604/20; 604/294; 600/383; 607/141

[58] Field of Search ................................ 604/20, 21, 289, 604/290, 294, 295, 301; 600/383; 607/141

[56] References Cited

U.S. PATENT DOCUMENTS

| | | |
|---|---|---|
| 2,525,381 | 10/1950 | Tower . |
| 4,109,648 | 8/1978 | Larke et al. ........................ 128/2.06 E |
| 4,564,016 | 1/1986 | Maurice et al. ......................... 128/645 |
| 5,174,304 | 12/1992 | Latina et al. . |
| 5,192,665 | 3/1993 | Salonen . |
| 5,498,521 | 3/1996 | Dryja et al. . |
| 5,522,864 | 6/1996 | Wallace et al. . |

FOREIGN PATENT DOCUMENTS

| | | |
|---|---|---|
| 325201 | 1/1989 | European Pat. Off. . |
| 641.745 | of 0000 | France . |
| 1489708 | 5/1969 | Germany . |

OTHER PUBLICATIONS

Behar–Cohen, Francine F., et al., "Iontophoresis of Dexamethasone in the Treatment of Endotoxin–Induced–Uveitis in Rats", *Exp. Eye Res.*, (1997) 65, 533–545.

Bradshaw, C.M., et al., "A Procedure for Comparing the Mobilities of Unlabeled Drugs Used in Microelectrophoresis Experiments", *Journal of Pharmacological Methods*, 5, 67–73 (1981).

McBrien, Neville A., et al., "Experimental Myopia in a Diurnal Mammal (*Sciurus Carolinensis*) With No Accommodative Ability", *Journal of Physiology*, (1993), 469, pp. 427–441.

Pirch, James H., et al., "A role for acetylcholine in conditioning–related responses of rat frontal cortex neurons: microintophoretic evidence", *Brain Research*, 586 (1992) 19–26.

Sarraf, David, et al., "The role of iontophoresis in ocular drug delivery", *Journal of Ocular Pharmacology*, vol. 10, No. 1: 69–81 (1994).

Yoshizumi, Marc O., et al., "Determination of Ocular Toxicity in Multiple Applications of Foscarnet Iontophoresis", *Journal of Ocular Pharmacology and Therapeutics*, (1997), 13:6, pp. 529–536.

*Primary Examiner*—John G. Weiss
*Assistant Examiner*—Michael Hayes
*Attorney, Agent, or Firm*—Garvey, Smith, Nehrbass & Doody, L.L.C.

[57] ABSTRACT

A contact lens with a conductive outer shell (one electrode of a two-electrode electrophoresis device) and a preferably soft, preferably disposable contact lens for contacting a patient's eye, assists in delivering dilation drops or other medicaments to a patient's eye. Advantageously, the lens is used with a relatively small hand-held power source. Electrophoresis can be used to help deliver dilation drops more rapidly, regardless of the delivery apparatus used for the electrophoresis.

10 Claims, 3 Drawing Sheets

DILATION ENHANCER

CROSS-REFERENCE TO RELATED APPLICATIONS

Not applicable.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to pupil dilation procedures. More particularly, the present invention relates to a method and apparatus for using electrophoresis to deliver pupil dilation and constriction agents.

2. General Background of the Invention

Every individual should have at least one dilated eye examination in adulthood. Many individuals with various eye problems such as macular degeneration, diabetes, threat of detached retina or history of detached retina as well as many other conditions require repeated dilated eye examinations. Dilated eye examinations typically require patients to wait several minutes after application of a dilator drug before the eye is sufficiently dilated for a dilated eye examination to occur.

Electrophoresis is an electrochemical process in which colloidal particles or molecules with a net electric charge migrate in a solution under the influence of an electric current. It is also sometimes called iontophoresis or cataphoresis. Electrophoresis is sometimes used now by others to deliver vitamins (such as Vitamin C) efficiently.

The following patents are incorporated herein by reference:

| U.S. Pat. Nos.: | 5,498,521 | 5,192,665 | 5,522,864 |
|---|---|---|---|
| | 5,174,304 | 2,525,381; | |

EP325,201; Fr.641,745; Germ. 1489708.

U.S. Pat. No. 2,525,381 discloses a contact lens type electrode holder. This electrode holder is used during ionic medication treatment of a patient's eye. The electrode itself has a relatively small surface area. The patent mentions "penicillin or other medicaments".

U.S. Pat. Nos. 5,174,304 and 5,222,864, Fr. Pat. No. 641,745, Germ. Pat. No. 1,489,708, and EP Pat. Office Publication No. 325,201 disclose electrodes for contacting eyeballs.

U.S. Pat. No. 5,498,521 discloses the use of a contact lens electrode placed on a topically anesthetized cornea after dilation of the pupils (see column 17, lines 13–16).

Also incorporated by reference are the following references:

Sarraf, David, et al., "The role of iontophoresis in ocular drug delivery", *Journal of Ocular Pharmacology*, vol. 10, no. 1: 69–81 (1994);

Pirch, James H., et al., "A role for acetylcholine in conditioning-related responses of rat frontal cortex neurons: microintophoretic evidence", *Brain Research*, 586 (1992) 19–26;

Behar-Cohen, Francine F., et al., "Iontophoresis of Dexamethasone in the Treatment of Endotoxin-Induced-Uveitis in Rats", *Exp. Eve Res.,* (1997) 65, 533–545;

Yoshizumi, Marc O., et al., "Determination of Ocular Toxicity in Multiple Applications of Foscarnet Iontophoresis", *Journal of Ocular Pharmacology and Therapeutics,* (1997), 13:6, pp.529–536;

Bradshaw, C. M., et al., "A Procedure for Comparing the Mobilities of Unlabeled Drugs Used in Microelectrophoresis Experiments", *Journal of Pharmacological Methods,* 5, 67–73 (1981);

McBrien, Neville A., et al., "Experimental Myopia in a Diurnal Mammal (*Sciurus Carolinensis*) With No Accommodative Ability", *Journal of Physiology,* (1993), 469, pp. 427–441.

BRIEF SUMMARY OF THE INVENTION

The apparatus of the present invention solves the problems confronted in the art in a simple and straightforward manner. What is provided is a dilation enhancer apparatus and method.

The dilation enhancer apparatus of the present invention is a hand held electrophoretic device using a contact lens type delivery system to provide rapid clinically useful dilation of the pupil of the eye. Other clinical applications may be useful.

The present invention comprises a contact lens with a conductive outer shell (one electrode of a two-electrode electrophoresis device) and a preferably soft, preferably disposable contact lens (made of a material such as polyfilcon, e.g. ocufilcon) for contacting a patient's eye. The present invention also comprises apparatus including the contact lens with the conductive outer shell and a relatively small hand-held power source. The present invention also comprises a method of using electrophoresis to help deliver dilation drops more rapidly, regardless of the means used for the electrophoresis.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

PARTS LIST

Figure 1:
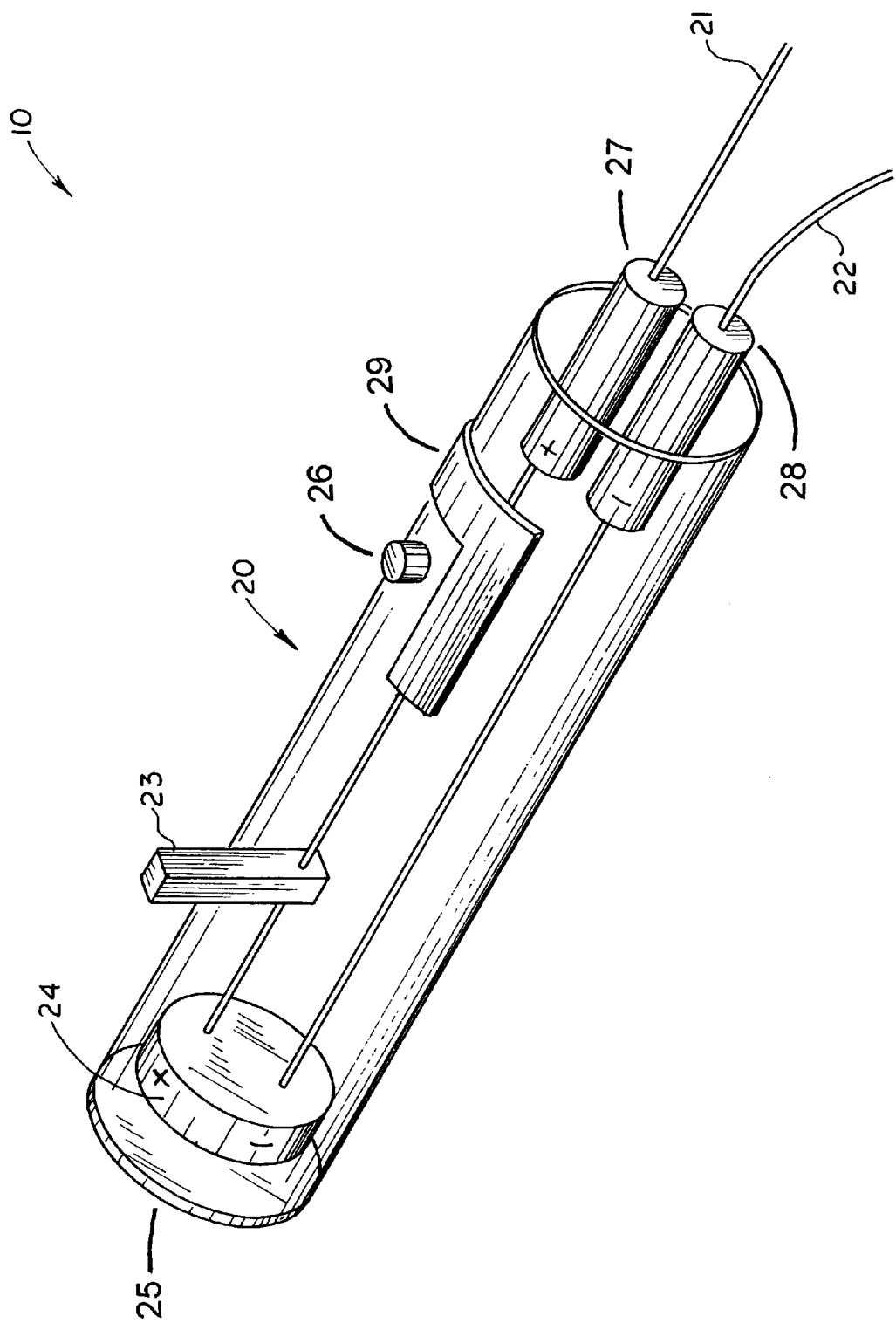
FIG. 1 is a perspective view of the preferred embodiment of the power supply apparatus of the present invention.
Figure 2:
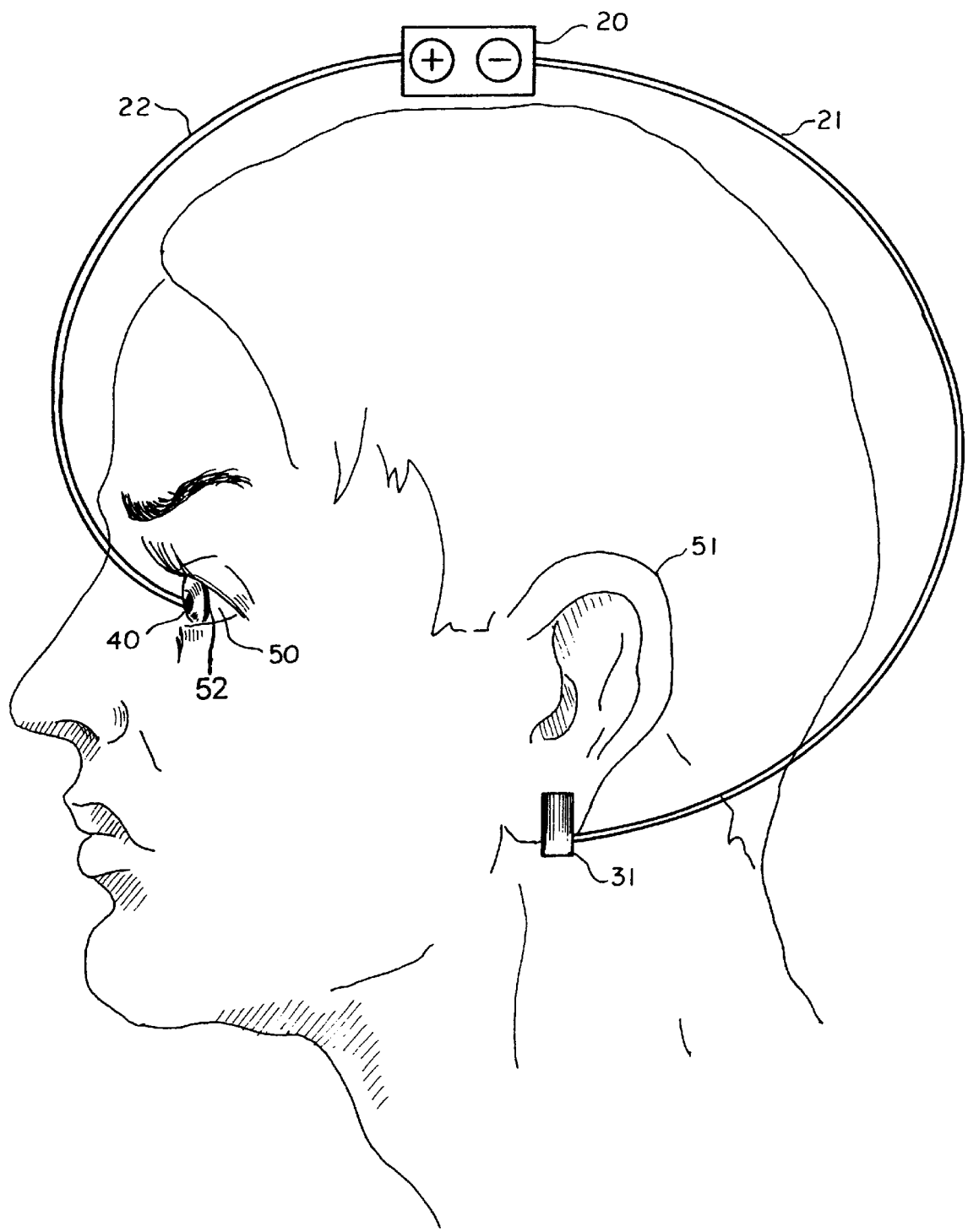
FIG. 2 shows the preferred embodiment of the apparatus of the present invention in use on a patient.
Figure 3A:
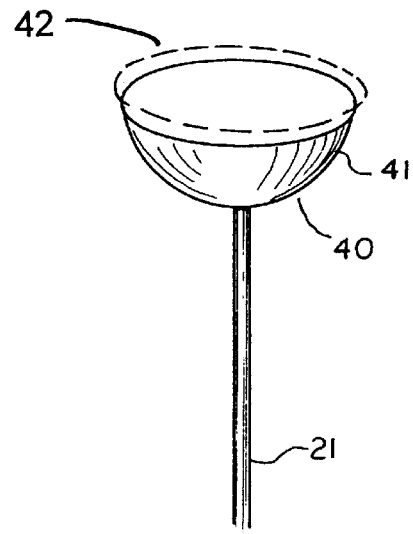
FIG. 3A is a side view of the preferred embodiment of the contact lens electrode apparatus of the present invention.
Figure 3B:
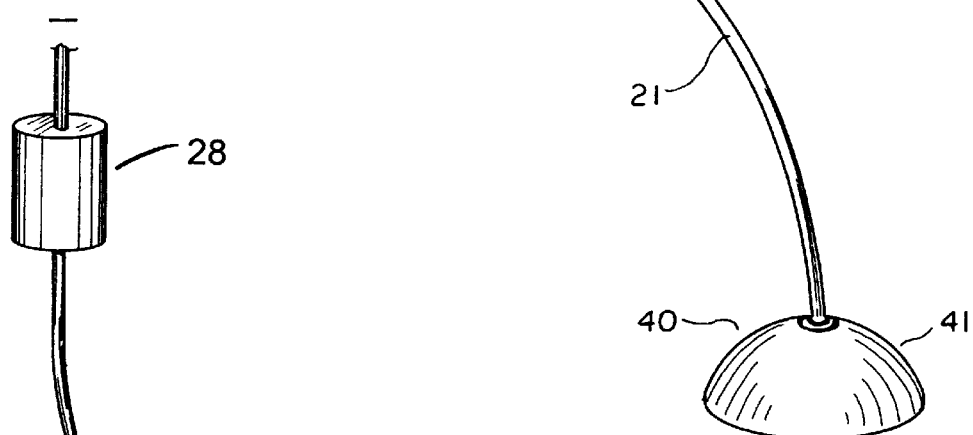
FIG. 3B is a top view of the preferred embodiment of the contact lens electrode apparatus of the present invention.
Figure 3:
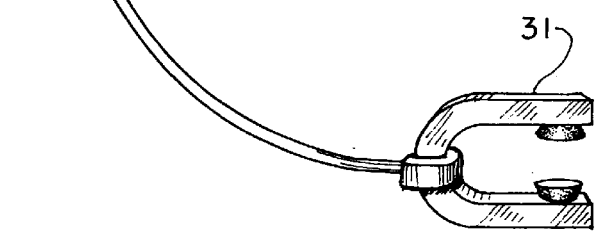
FIG. 3 is a side view of the preferred embodiment of the earlobe clamp apparatus of the present invention.

10 dilation enhancer of the present invention
20 hand-held iontophoretic power source (dilation enhancer power supply)
21 positive wire electrode (to eye)
22 negative wire electrode (to ear)
23 "on/off" switch (starter, reset)
24 battery with 1 milliamp output 25 battery access cover
26 "on" light and elapsed timer
27 positive receptacle
28 negative receptacle
29 timer with automatic one minute shutoff
30 reference electrode (conductive comfortable earlobe clamp with conductive padding)
40 conductive contact lens
41 conductive shell preferably made of metal or other suitable material (such as plastic) (reusable, sterilizable)
42 preferably disposable soft contact lens (polymer type)
50 patient's eye
51 patient's ear
52 patient's limbus

DETAILED DESCRIPTION OF THE INVENTION

The present technique consists of topically applying one or more eye drops of particular compounds that either stimulate the dilator muscle of the iris or paralyze the constricting sphincter muscle of the iris to produce pupillary dilation. The usual time is at least 20 minutes and may be considerably longer in order to achieve clinically useful dilation to promote examination.

The dilation enhancer 10 of the present invention uses a novel contact delivery system operated through a hand-held iontophoretic power source 20 to deliver efficacious amounts of dilating drugs across the cornea of the eye 50 to bathe the iris of the eye 50 very rapidly achieving a rapid, complete, clinically useful dilation.

The same technique can be used with other compounds to produce a reversal of the dilation much more rapidly than by the prior technique of topical drop application.

Description of the Device:

In the present invention, iontophoresis employs a current flow at low amperage from a positive electrode across tissues enhanced by the presence of a reference electrode 31 clamped onto the patient's ear 51.

The power supply 20 is constructed with internal regulation such that there is a steady output of a predetermined (preferably one milliamp) current. The current is delivered through wire electrodes 21, 22 to a conductive contact lens 40. Conductive contact lens 40 includes a conductive shell 41 preferably made of metal or other suitable material (such as plastic) and preferably reusable and sterilizable, having a diameter appropriate for a patient's eye (such as about 10 mm) and a preferably disposable soft contact lens 42 which fits in the conductive shell 41 and has a similar diameter (such as about 11 mm). The combination of shell 41 and lens 42 can define a composite contact lens.

The hand held device has an "on/off" switch 23. It is preferably battery 24 powered.

Example of Operation of the Device:

After the patient is informed of what sensations to expect, a single topical anesthetic drop is applied to each eye.

The electrophoretic contact lens 40 is charged with one drop each of 2.5% Phenylephrine and 1% Tropicamide. The contact lens 40 is applied corneal surface down to the cornea with the patient's lids supported open. The current is switched on and the contact lens 40 left in place for a period of 90 seconds. At the end of the 90 seconds, the contact lens is removed. The eye is observed for another 60 seconds and should show substantial if not full dilation. If less than optimal dilation is achieved, the process can be repeated.

The same sequence is carried out for the other eye.

At the end of examination, a dilation reversing drop is used to charge the contact lens corneal side. Electrophoresis is again switched on for a period of 90 seconds. The patient then receives an artificial tear drop and should be comfortably ready to be discharged from the office or other venue.

Possible Risks and Benefits:

Using the current of one milliamp, no corneal surface or stroma problems have been noted.

The direction of the current across the cornea and the wide spread area of application of the current minimizes the likelihood of any tissue damage and keeps the electrophoretic current away from other tissues such as ciliary body and retina.

The major benefit of the device is allowing the patient to undergo a dilated examination within a very short time after concluding any undilated examination, eliminating the protracted wait for dilation to occur. The technique also provides wider dilation than is achievable even by repeated drop application.

The apparatus of the present invention can also be used for corneal antibiotic or other drug delivery.

The device of the present invention may also be useful for preliminary testing of responsiveness to antiocular hypotensive drugs, currently now a laborious process for practitioner and patient involving repeat visits spaced out over weeks of time.

Experiments to prove efficacy of the present invention:

PURPOSE:

To determine the pupillary dilation efficacy of Iontophoresis vs. Topical Application of: a) Phenylephrine 2.5% and b) Tropicamide 1%. Also to determine the dilation reversal efficacy of RevEyes and Pilocarpine 2%.

METHODS:

Experiment I—4 rabbits used

1) Drug added by applying one drop to right eye then observing pupillary changes at 0, 2 minutes, 5 minutes and 10 minutes.
2) Drug to other eye added by electrophoresis at 4 mA for 2 minutes. Pupillary changes monitored as above.

Experiment II—4 rabbits used

1) One drop added and pupillary changes monitored at 0, 2 minutes, 5 minutes and 10 minutes.
2) To the other eye Phenylephrine electrophoresis at 1 mA for 2 minutes. Pupillary changes monitored as above.

Experiment III—4 rabbits used

1) Both eyes subjected to electrophoresis of Phenylephrine or Tropicamide at 1 mA for 2 minutes.
A) One eye received 1 drop of RevEyes or Pilocarpine and pupillary changes monitored.
B) Other eye electrophoresis of RevEyes or Pilocarpine at I mA for 2 minutes.

NOTE: Addition of RevEyes or Pilocarpine by drop; small changes seen at 10 minutes; at 20 minutes pupils were more nearly normal by still about 6 mm ("normal" is about 4 mm). Pupil dilation was observed at 2 minutes with electrophoresis of Phenylephrine at 4 mA or 1 mA. The 1 mA was most comfortable for the animal. There was no increase in heavy breathing or heart rate as with 4 mA. Addition of drop application did not fully dilate pupils until the 10 minute time point and pupil was still not fully dilated until 20 minutes.

|  | Pupil diameter (mm) at: | | | | |
| --- | --- | --- | --- | --- | --- |
|  | 0 time | 2 min. | 5 min. | 10 min. | 20 min. |
| 2.5% Phenylephrine | | | | | |
| Drop | 4 | 4 | 5 | 8 | |
| Electro. | 4 | 8 | 8 | 10 | |
| RevEyes | | | | | |
| Drop | 9 | 9 | 9 | 9 | 9 |
| Electro. | 10 | 9 | 9 | 8 | 6 |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

What is claimed is:

1. Apparatus for dilating a patient's pupil comprising:
   a composite contact lens structure that comprises:
      a conductive outer shell with a concavity; and
      a lens that fits the concavity of the shell, for contacting a patient's eye; and
      a dilation drug liquid that forms an interface between the patient's eye and the lens.
2. The apparatus of claim 1, wherein the lens is soft.
3. The apparatus of claim 2, wherein the lens is made of polyfilcon.
4. The apparatus of claim 1, further comprising a hand-held power source.
5. The apparatus of claim 4, wherein the power source is battery powered.
6. The apparatus of claim 1 wherein the lens is disposable.
7. The apparatus of claim 1 wherein the lens removably fits the shell.
8. The apparatus of claim 1 wherein the shell has a convex portion with an electrode thereon.
9. A method of delivering dilation drops to a patient for dilating the patient's pupil more rapidly, comprising the steps of:
   a) placing a contact lens on the patient's eye applying dilation drops to a patient's eye and in between the patient's eye and the lens;
   b) applying electrical current of not more than 1.5 mA to the patient's eye for not more than 120 seconds.
10. A method of dilating a patient's pupil, comprising the steps of:
   a) placing a contact lens on the patient's eye applying dilation drops to a patient's eye and in between the patient's eye and the lens
   b) applying iris constriction drops to a patient's eye in between the patient's eye and the lens and
   c) applying electrical current of not more than 1.5 mA to the patient's eye for not more than 120 seconds.

* * * * *